United States Patent [19]
Rogers et al.

[11] Patent Number: 5,731,410
[45] Date of Patent: Mar. 24, 1998

[54] PEPTIDE FOR BLOCKING AUTOANTIBODY-EVOKED ACTIVATION OF GLUTAMATE RECEPTOR TYPE 3 (GLUR3)

[75] Inventors: Scott W. Rogers; Lorise C. Gahring, both of Salt Lake City; Roy E. Twyman, Sandy, all of Utah

[73] Assignee: University of Utah Research Foundation, Salt Lake City, Utah

[21] Appl. No.: 345,527

[22] Filed: Nov. 28, 1994

[51] Int. Cl.⁶ .......................... C07L 14/435; A61K 38/16
[52] U.S. Cl. .......................................................... 530/325
[58] Field of Search ................................. 530/300, 325, 530/350, 389

[56] References Cited

PUBLICATIONS

Wenthold et al, Journal of Biological Chemistry, 267 (1) 501–507, Jan. 5. 1992.
Boulter et al, Science, vol. 249: 1033–1037, 31 Aug. 1990.

*Primary Examiner*—Marianne P. Allen
*Assistant Examiner*—Patricia A. Duffy
*Attorney, Agent, or Firm*—Thorpe, North & Western, L.L.P.

[57] ABSTRACT

A peptide containing 24 amino acid residues that binds to anti-neuronal-glutamate-receptor autoantibodies associated with Rasmussen's encephalitis and that blocks activation of the GluR3 subunit is described. Methods of making the peptide and treating Rasmussen's encephalitis are also disclosed. Autoantibodies to other glutamate receptor subunits are associated with paraneoplastic neurodegenerative disease, amyotrophic lateral sclerosis, and neurodegenerative disease of unknown diagnosis. Methods of screening patients and of monitoring patients being treated for these disorders and syndromes are further described.

1 Claim, 6 Drawing Sheets

Fig. 1

```
                        1                                           5                                          10                                         15
GluR1 (SEQ ID NO:3)    Asn Tyr Thr Asp Thr Ile Pro Ala Arg Ile Met Gln Gln Trp Arg Thr
GluR2 (SEQ ID NO:4)    Asp Tyr Asp Asp Ser Leu Val Ser Lys Phe Ile Glu Arg Trp Ser Thr
GluR3 (SEQ ID NO:1)    Asn Asn Glu Asn Pro Met Val Gln Gln Phe Ile Gln Arg Trp Val Arg 20                                         25
GluR1                  Ser Asp Ser Arg Asp His Thr Arg Val Asp Trp Lys Arg
GluR2                  Leu Glu Glu Lys Glu Tyr Pro Gly Ala His Thr Ala Thr
GluR3                  Leu Asp Glu Arg Phe Pro Glu Ala Ala Lys Asn Ala Pro
```

|  | 1 | | | | 5 | | | | | 10 | | | | | 15 |
|---|---|---|---|---|---|---|---|---|---|---|---|---|---|---|---|
| GluR1 (SEQ ID NO:5) | Asn | Glu | Asp | Lys | Phe | Val | Pro | Ala | Thr | Asp | Ala | Gln | Ala | Gly |
| GluR2 (SEQ ID NO:6) | Ser | Glu | Val | Asp | Lys | Met | Val | Thr | Leu | Glu | Leu | Pro | Ser | Gly |
| GluR3 (SEQ ID NO:2) | Asn | Glu | Tyr | Glu | Arg | Phe | Val | Pro | Phe | Ser | Asp | Gln | Gln | Ile | Ser |

|  | | | | | 20 | | | | | 25 |
|---|---|---|---|---|---|---|---|---|---|---|
| GluR1 | Gly | Asp | Asn | Ser | Val | Gln | Asn | Arg |
| GluR2 | Asn | Asp | Thr | Ser | Gly | Leu | Glu | Asn | Lys |
| GluR3 | Asn | Asp | Ser | Ser | Ser | Glu | Gly | Asn | Arg |

Fig. 2

PEPTIDE FOR BLOCKING AUTOANTIBODY-EVOKED ACTIVATION OF GLUTAMATE RECEPTOR TYPE 3 (GLUR3)

This invention was made with government support under Grant Nos. NS30990 and NS531519 awarded by the National Institutes of Health. The government has certain rights in the invention.

BACKGROUND OF THE INVENTION

This invention relates to neurological disorders and neurodegenerative syndromes with an autoimmune component. More particularly, this invention relates to compositions and methods for diagnosis and treatment of neurological disorders and neurodegenerative syndromes wherein autoantibodies to one or more neuronal glutamate receptor subunits are associated with the disorders and syndromes.

Neurological disorders and neurodegenerative syndromes afflict an alarming number of individuals and present an increasing economic challenge to the health care system since little is known regarding their causes, their diagnosis is often subjective, and many lack effective treatment. Mental activity is ultimately determined by the capacity of neurons to communicate at synapses. The location of neurotransmitter receptors at synapses makes them a likely target for alterations during aging and in diseases that alter behavior and cognition. Among these many receptor types are the neuronal glutamate receptors (GluR's), γ-aminobutyric acid receptors (GABAR's), nicotinic acetylcholine receptors, serotonin receptors, dopamine receptors, and the like.

GluR's comprise the predominant fast excitatory neurotransmitter system in the mammalian central nervous system and could play a role in the etiology of some forms of disease thereof. D. Choi, 23 J. Neurobiol. 1261 (1992). For example, excessive glutamate receptor stimulation has been linked to subsequent neuronal death. This excitotoxicity is thought to play a role in nervous system destruction after stroke, trauma, epilepsy, Alzheimer's disease, and Huntington's disease.

Similar to other ligand-activated ion channels, there are numerous subunits that compose the glutamate receptor family. The number of native GluR's is unknown, and the potential diversity of these receptors is immense. Sixteen subunits of the glutamate receptor have been molecularly cloned to date. M. Hollmann & S. F. Heinemann, *Cloned Glutamate Receptors*, 17 Ann. Rev. Neurosci. 31–108 (1993). Currently, these subunits are broadly grouped on the basis of sequence identity and response to agonists when expressed as a receptor in *Xenopus oocytes* or in transfected cells. These divisions include cDNAS that encode receptors with N-methyl-D-aspartate (NMDA) pharmacology and at least 9 cDNAs that encode non-NMDA receptor types. This latter group can be subdivided into three groups based upon similarity of primary sequence and/or function. GluR1, GluR2, GluR3, and GluR4 form receptors that are responsive to kainic acid and α-amino-3-hydroxy-5-methyl-4-isoxazole propionate (AMPA) and bind AMPA with high affinity. GluR5, GluR6, and GluR7 form receptors that are responsive to kainic acid or bind kainic acid with high affinity. KA1 and KA2 do not function alone, but form high affinity kainic acid binding sites or kainate/AMPA responsive receptors when expressed with other GluR subunits in cultured cells.

Rasmussen's encephalitis is a childhood disease of intractable focal seizures and characteristic inflammatory histopathology in the affected brain hemisphere. Two rabbits injected with a bacterial fusion protein expressing a portion of a glutamate receptor subunit, GluR3, were observed to develop seizures and early histopathological changes similar to those observed in Rasmussen's encephalitis. To test the hypothesis that an autoimmune response to GluR3 is associated with Rasmussen's encephalitis, sera from affected patients and age and sex matched controls were examined for immunoreactivity to GluR subunits using immunoblot analysis and transfected cells expressing GluR3. Rasmussen patients with active disease were found to have circulating IgG antibodies to GluR3. In a therapeutic trial of one patient, removal of circulating GluR3 antibodies by plasmapheresis correlated with a reduced rate of seizure and improved cognitive function. S. Rogers et al., Autoantibodies to Glutamate Receptor GluR3 in Rasmussen's *Encephalitis*, 265 Science 648 (1994); U.S. Pat. No. 5,529,898.

Although thought to play a role in neurological disease, the mechanism underlying the role of such receptors is obscure. The majority of current research seeks to identify drugs that act upon these receptors directly or that modify cellular processes in the brain to maintain the correct expression of these receptors.

In view of the foregoing, it will be appreciated that compositions and methods for screening and treating neurological disorders and neurodegenerative syndromes would be significant advancements in the art.

OBJECTS AND SUMMARY OF THE INVENTION

It is an object of the present invention to provide a composition and method of use thereof for screening of epilepsies including Rasmussen's encephalitis, paraneoplastic syndromes, amyotrophic lateral sclerosis, neurodegenerative disorders, and inflammatory diseases of the nervous system.

It is also an object of the invention to provide a method of screening a neurological disorder or neurodegenerative syndrome wherein immunoreactivity to one or more subunits of the neuronal glutamate receptor is associated therewith.

It is another object of the invention to provide a method of treating a neurological disorder or neurodegenerative syndrome wherein immunoreactivity to one or more subunits of the neuronal glutamate receptor is associated therewith.

These and other objects can be achieved by a peptide or other expressed protein comprising a sequence of amino acids identified herein as SEQ ID NO:2 and sequences substantially homologous therewith, wherein said peptide is capable of binding anti-GluR3 autoantibodies and blocking the ability of said anti-GluR3 autoantibodies to activate GluR3 in neuronal cells.

A method of making a peptide for treating a neurological disorder or neurodegenerative syndrome, such as Rasmussen's encephalitis, wherein autoantibodies to a neuronal glutamate receptor subunit are associated therewith, comprises the steps of identifying the glutamate receptor subunit to which the autoantibodies are directed; comparing amino acid sequences of the identified glutamate receptor subunit and a related glutamate receptor subunit; identifying a segment of the identified glutamate receptor subunit having substantial sequence divergence from an equivalent region of the related glutamate receptor subunit; synthesizing a peptide having an amino acid sequence corresponding to the identified segment of substantial sequence divergence; and testing the synthesized peptide for ability to bind to said autoantibodies and thereby block activation or enhancement of activity of said glutamate receptor subunit.

A method of screening a patient for a neurological disorder or neurodegenerative syndrome wherein autoantibodies to a neuronal glutamate receptor subunit are associated therewith comprises obtaining a biological sample from the patient, and detecting the autoantibodies to the neuronal glutamate receptor subunit in the biological sample, wherein the presence of the autoantibodies signifies that the patient has or is at risk for the neurological disorder or neurodegenerative syndrome. Autoantibodies can be detected by a physical assay, such as immunoblot assay, immunocytochemistry of transfected cells, ELISA, competitive peptide ELISA, radiodiffusion assay, Ouchterlony plate assay, radioimmunoassay, rocket immunoelectrophoresis, and the like. A functional assay, such as electrophysiological measurement of receptor activity, used with the physical assay improves reliability. Screening of Rasmussen's encephalitis is by detecting autoantibodies to at least the GluR3B region of GluR3, but the GluR3A or the intact GluR3 fragment or receptor may also be used. Screening of paraneoplastic neurodegenerative disease is by detecting autoantibodies to GluR1 and GluR5 and/or GluR6. Screening of amyotrophic lateral sclerosis is by detecting autoantibodies to GluR2, with a subset of patients also having autoantibodies to GluR5 and/or GluR6. A neurodegenerative disease of unknown diagnosis was also found to be associated with autoantibodies to glutamate receptor subunits.

A method of monitoring a neurological disorder or neurodegenerative syndrome wherein autoantibodies to a neuronal glutamate receptor subunit are associated therewith comprises the steps of collecting a first biological sample from a patient who is to be treated; determining the amount of autoantibodies to the glutamate receptor subunit in the first biological sample; collecting a second biological sample from the patient after the patient has been treated for the disorder or syndrome; determining the amount of autoantibodies to the glutamate receptor subunit in the second biological sample; and comparing the amounts determined in the first and second biological samples.

A method of treating a neurological disorder or neurodegenerative syndrome wherein autoantibodies to a neuronal glutamate receptor subunit are associated therewith comprises systemically administering an effective amount of a peptide operable for binding the autoantibodies and blocking autoantibody-evoked activation or enhancement of activity of the glutamate receptor subunit. For treating Rasmussen's encephalitis, the peptide is GluR3B or peptides substantially homologous thereto.

BRIEF DESCRIPTION OF THE DRAWINGS

FIG. 1 shows amino acid sequence alignments of GluR3A (SEQ ID NO.:1) with corresponding regions in GluR1 (SEQ ID NO.:3) and GluR2 (SEQ ID NO.:4).

FIG. 2 shows amino acid sequence alignments of GluR3B (SEQ ID NO.:2) with corresponding regions in GluR1 (SEQ ID NO:5) and GluR2 (SEQ ID NO:6).

DETAILED DESCRIPTION OF THE INVENTION

Figure 3:
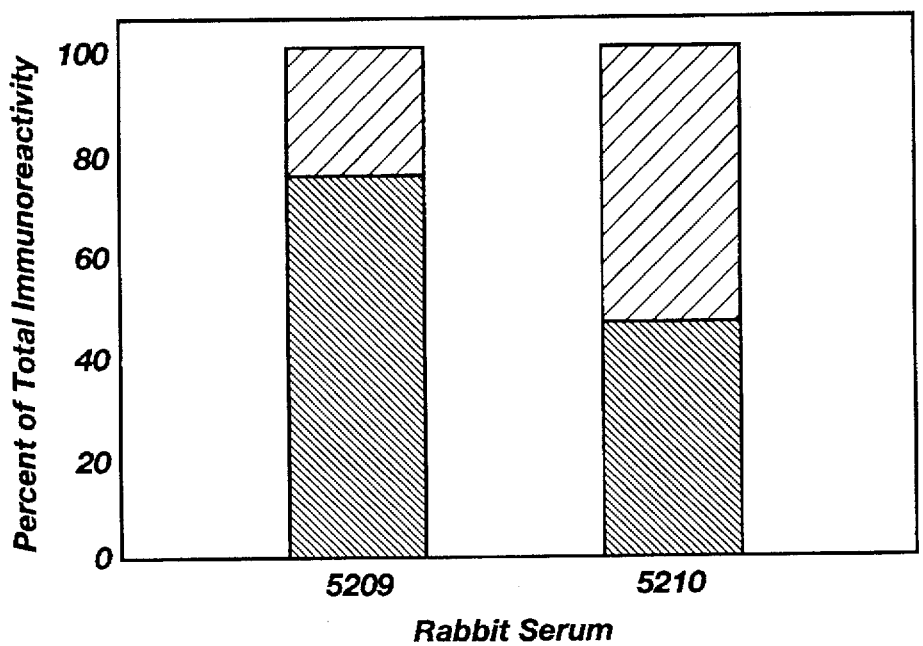
FIG. 3 shows the proportion of immunoreactivity of sera, as determined by ELISA, from two rabbits (5209 and 5210) immunized with a trpE-GluR3 fusion protein to synthetic peptides corresponding to the sequences identified as GluR3A (hatched bars; SEQ ID NO:1) and GluR3B (solid bars; SEQ ID NO:2).

Before the present compositions and methods for screening, monitoring, and treating neurological disorders and neurodegenerative syndromes are disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the content clearly dictates otherwise. Thus, for example, reference to a composition containing "a peptide" includes a mixture of two or more peptides, reference to "an antibody" includes reference to one or more of such antibodies, and reference to "a drug" includes reference to a mixture of two or more drugs.

In describing and claiming the present invention, the following terminology will be used in accordance with the definitions set out below.

As used herein, "antibody" means an immunoglobulin molecule that interacts only with the antigen that induced its synthesis in lymphoid tissue and/or cells or with antigens closely related to it. included within this definition of antibody all antibody types, e.g., IgG, IgA, IgM, etc.; IgG subclasses, e.g., IgG1, IgG2, etc.; F(ab) fragments; F(ab)$_2$ fragments; light chain dimers; and the like. This definition also includes antibodies that react with low or high affinity with an antigen.

As used herein, "biological sample" means a sample of biological material taken from a patient for performing an assay thereon for determining whether autoantibodies against glutamate receptor subunits are present in the patient's body and/or the quantity or concentration of such autoantibodies. Preferred biological samples are biological fluids, such as blood, blood plasma, cerebrospinal fluid, and the like.

As used herein, "physical assay" means an assay that determines the physical presence of autoantibodies in a biological sample. Physical assays can be used for making qualitative and quantitative measurements of autoantibodies. Preferred physical assays include immunoblot, immunocytochemistry of transfected cell, ELISA, and competitive peptide ELISA assays and the like. "Functional assay" means an assay that determines the presence of autoantibodies in a biological sample by the ability of the autoantibodies to perform some measurable function. For example, autoantibodies to the GluR3 subunit of the glutamate receptor activate GluR inward currents, and such inward currents can be detected and measured by electrophysiological methods. Thus, such electrophysiological methods are functional assays of the presence of autoantibodies in a sample.

As used herein, "substantial sequence divergence" means significant difference in primary structure of amino acid sequences being compared. For example, amino acids 245–457 of the GluR3 protein are 64% identical to the equivalent region of the GluR2 protein. The GluR3B segment, comprising amino acids 372–395, however, is only 28% identical to the equivalent region of the GluR2 protein. The GluR3B segment, therefore, exhibits substantial sequence divergence from the equivalent region in GluR2.

As used herein, "effective amount" means an amount capable of producing a selected effect. Thus, an effective amount of a peptide capable of binding certain autoantibodies and blocking autoantibody-evoked activation or enhancement of activity of a particular glutamate receptor subunit is an amount that produces this selected effect. Such an effective amount can be determined by a person of ordinary skill in the art without undue experimentation.

As used herein, "peptide" means peptides of any length and includes proteins. The terms "polypeptide" and "oligopeptide" are used herein without any particular intended size limitation, unless a particular size is otherwise stated.

As used herein, a "substantially homologous" peptide to GluR3B means a peptide that retains functionality in binding anti-GluR3 autoantibodies and in blocking the ability of such autoantibodies to activate the GluR3 subunit, although it may include flanking sequences or be a truncation, deletion variant, or substitution variant of SEQ ID NO:2. The minimum requirement for functionality is not currently known. A substitution variant is one that contains a conservative substitution of one or more amino acid residues. A conservative substitution is a substitution of one amino acid for another wherein functionality of the peptide is retained. Amino acid residues belonging to certain conservative substitution groups can sometimes substitute for another amino acid residue in the same group. Substitution groups have been variously defined, however, one such definition is as follows: Pro; Ala, Gly; Ser, Thr; Asn, Gln; Asp, Glu; His; Lys, Arg; Cys; Ile, Leu, Met, Val; and Phe, Trp, Tyr. M. Jimenez-Montano & L. Zamora-Cortina, *Evolutionary Model for the Generation of Amino Acid Sequences and its Application to the Study of Mammal Alpha-Hemoglobin Chains*, Proc. VIIth Int'l Biophysics Congress, Mexico City (1981). Other variations that are to be considered substantially homologous include substitution of D-amino acids for the naturally occurring L-amino acids, substitution of amino acid derivatives such as those containing additional side chains, and substitution of non-standard amino acids, i.e. α-amino acids that are rare or do not occur in proteins. The primary structure of a peptide substantially homologous to GluR3B is limited only by functionality. Short peptides are generally preferred, however, both because short peptides can be manipulated more readily and because the presence of additional amino acid residues, and particularly of substantial numbers of additional amino acid residues, may interfere with the function of the peptide.

Traditionally, the brain is viewed as an immune-privileged region of the body. This means that immune mediators such as antibodies should not have active access to the brain. Although autoimmune diseases of the nervous system are known (e.g., multiple sclerosis, MS) that affect neurotransmission through disruption of the function of major structural proteins such as myelin, it is not intuitively obvious that autoimmunity to specific neurotransmitter receptors, such as glutamate receptors (GluR's) may be a generalized mechanism underlying numerous neurological disorders.

Rasmussen's Encephalitis

As mentioned above, previous work suggests that Rasmussen's encephalitis contains an autoimmune component that includes autoreactive antibodies to glutamate receptors of the central nervous system. Rogers et al., *Autoantibodies to Glutamate Receptor GluR3 in Rasmussen's Encephalitis*, 265 Science 648 (1994); U.S. patent application Ser. No. 08/109,234. Autoantibodies to a specific glutamate receptor subunit, GluR3, were detected in sera of patients with active Rasmussen's encephalitis. Removal of anti-GluR3 antibodies by plasmapheresis correlated with reduced number of seizures. Further, two rabbits immunized with bacterially expressed fusion proteins of trpE with a portion of the putative extracellular domain of GluR3 exhibited behavioral characteristics indicative of seizure activity after development of high titers of anti-GluR3 antibodies. Histopathological features similar to those of Rasmussen's encephalitis were also found in these rabbits.

In the present invention, pathophysiological mechanisms underlying an interaction of an antibody and ion channel receptor protein have been studied. Anti-GluR3 subtype-specific antibodies were generated by immunizing rabbits with bacterially expressed trpE-GluR3 fusion proteins that included a portion of the putative extracellular domain of GluR3, according to S. Rogers et al., 11 J. Neurosci. 2713 (1991); S. Rogers et al., 12 J. Neurosci. 4611 (1992), hereby incorporated herein by reference.

Anti-GluR3 serum was used to label human embryonic cells transfected with GluR1, GluR2, GluR3, or GluR6 cDNAs. M. Hollmann & S. F. Heinemann, *Cloned Glutamate Receptors*, 17 Ann. Rev. Neurosci. 31–108 (1993). HEK 293 cells (ATCC CRL 1573) were transfected with the cDNAs as in S. Rogers et al., 11 J. Neurosci. 2713 (1991); S. Rogers et al., 12 J. Neurosci. 4611 (1992); G. Huntley et al., 13 J. Neurosci. 2965 (1993), hereby incorporated by reference. immunocytochemical detection of antigen expressed from the transfected cDNAs was performed by fixing the cells, permeabilizing them with detergent, exposing them to anti-GluR3 serum so that anti-GluR3 antibodies attach to the fusion protein, binding the anti-GluR3 antibodies with a secondary antibody (e.g., alkaline phosphatase-conjugated goat anti-human antibody), and adding colorigenic substrates. Only cells transfected with GluR3 cDNA were labeled by the rabbit serum. Similar results were obtained with serum from rabbit 5210 that exhibited seizures following injection with GluR3 antigen, S. Rogers et al., 265 Science 648 (1994).

Comparison of the amino acid sequence of the trpE-GluR3 fusion protein (containing amino acids 245–457 of the GluR3 protein) with the equivalent regions of GluR1 and GluR2 revealed that the GluR1 and GluR2 sequences are, respectively, 60% and 64% identical to the GluR3 sequence. There are, however, two regions of substantial sequence divergence (FIGS. 1 and 2). These two divergent regions comprise amino acids 245–274 (GluR3A; SEQ ID NO:1) and 372–395 (GluR3B; SEQ ID NO:2), respectively. GluR3A is, respectively, only 17% and 38% identical to the equivalent regions of GluR1 and GluR2, and GluR3B is, respectively, only 48% and 28% identical to the equivalent regions of GluR1 and GluR2.

Peptides containing these two amino acid sequences were synthesized, e.g., B. Merrifield et al., 21 Biochemistry 5020–31 (1982); Houghten, 82 Proc. Nat'l Acad. Sci. USA 5131–35 (1985), and analyzed for immunoreactivity with rabbit anti-GluR3 antiserum using an immobilized peptide ELISA, according to the procedure of S. Rogers et al., 11 J. Neurosci. 2713 (1991); S. Rogers et al., 12 J. Neurosci. 4611 (1992); G. Huntley et al., 13 J. Neurosci. 2965 (1993); E. Harlow & D. Lane, *Antibodies: A Laboratory Manual* (1988). These peptides could also be synthesized by methods of recombinant DNA technology, as is known in the art, e.g., J. Sambrook et al., *Molecular Cloning: A Laboratory Manual* (2d ed., 1989). FIG. 3 shows that sera from both rabbits exhibited immunoreactivity to both synthetic peptides although relative reactivity to the two peptides differed between the two sera. These results demonstrate that at least two peptides with low sequence identity to closely related GluR1 and GluR2 subunits contain epitopes recognized by the anti-GluR3-specific rabbit antiserum.

To examine functional consequences of antibody binding to glutamate receptors, electrophysiological methods were used to record whole cell currents from mouse cortical neurons in culture. Neuronal cultures from fetal (E14-16) mouse cortical and hippocampal structures were prepared on poly-L-lysine-coated 35 mm "FALCON" dishes according to G. Skeen et al., 44 Molec. Pharmacol. 443 (1993), hereby incorporated by reference. Cultures were fed every other day using a growth medium consisting of DMEM, 10% horse serum, 30 mM glucose, and 0.5 mM glutamine. Arabinosylcytosine (ARA-C) was added for 1 day during the first week in culture to suppress growth of non-neuronal cells. Electrophysiological experiments were performed on 2–5 week old cultures at room temperature. External solution consisted of 145 mM NaCl, 1.5 mM KCl, 1 mM $CaCl_2$, 1 mM $MgCl_2$, 10 mM Na-HEPES, 10 mM glucose, 30 mM sucrose at pH 7.4, 320 mOsm. Internal solution consisted of 153 mM CsCl, 10 mM Cs-HEPES, 4 mM $MgCl_2$, 5 mM EGTA at pH 7.35, 300 mOsm. Solutions were designed for measurement of predominantly sodium inward currents and to block NMDA receptor currents when neurons are voltage clamped at −75 mV. No current was evoked by 100 μM NMDA with 1 μM glycine using this paradigm. To block other currents, 0.2–1 μM tetrodotoxin (TTX), 10 μM picrotoxin, 10 nM strychnine were added to the external solution. External solution was perfused continuously at about 2 ml/min. Purified sera or IgG ligands were kept on ice until immediately before use and diluted into external solution. Ligands were applied to cells by 2 sec pressure ejection using blunt miniperfusion pipettes (about 20 μm diameter) about 100 μm from the cell. Miniperfusion pipettes were filled and the contents ejected three times with ligand solution to reduce effects of protein binding to glass. Recordings were obtained with an Axon Instruments 200A amplifier using borosilicate glass electrodes (2.5–4 MΩ). Membrane currents were filtered at 500 Hz and digitized at 2 kHz. TTX, picrotoxin, strychnine, NMDA, glycine, and salts were obtained from Sigma Chemical Co. (St. Louis, Mo.). Kainic acid, MK-801, and 6-cyano-7-nitroquinoxaline-2,3-dione (CNQX) were obtained from Research Biochemicals international (Natick, Mass.).

Figure 4:
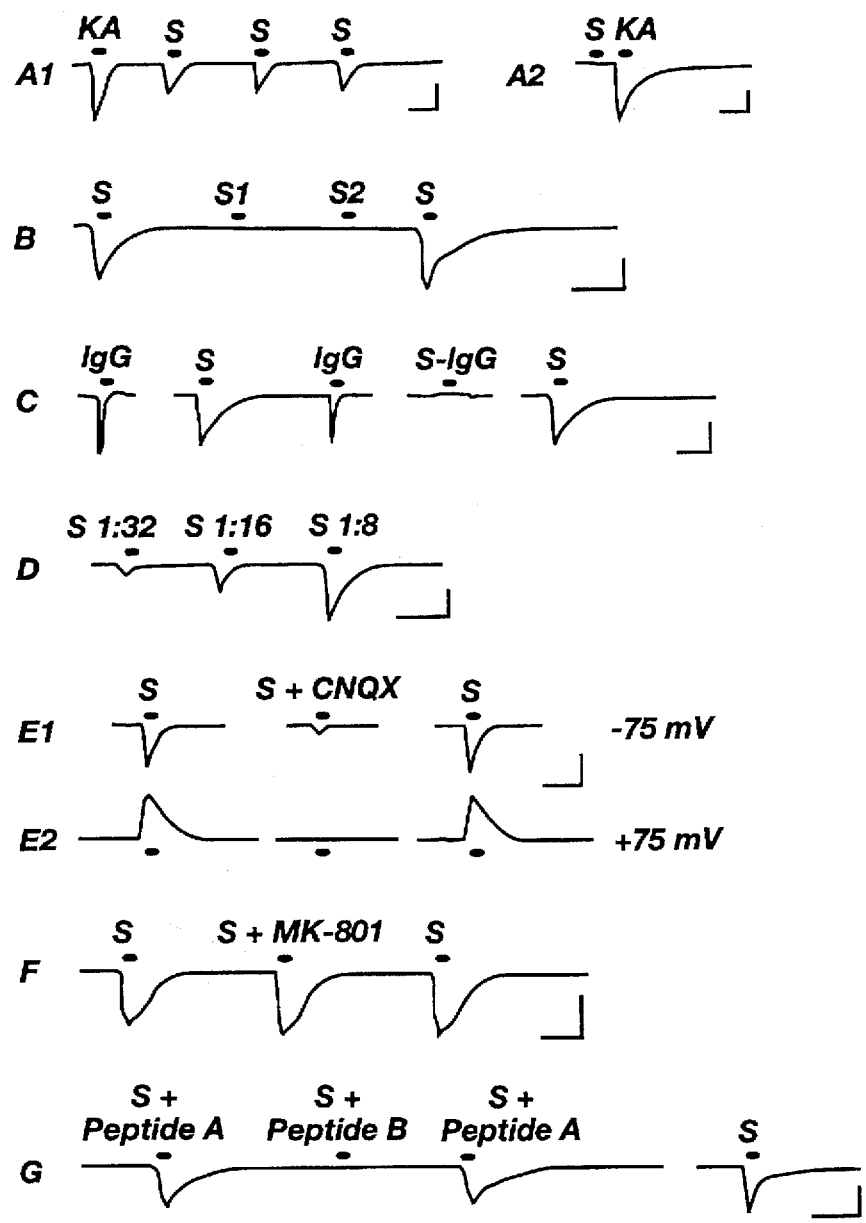
FIG. 4 shows anti-GluR3 antibody-evoked whole cell currents recorded from voltage-clamped fetal mouse cortical neurons in culture. Serum containing anti-GluR3 antibody (S) is from rabbit 5209 and applied at 1:8 dilution unless otherwise noted. Calibration bars are 10 sec and 500 pA. In (A), there is shown a comparison of currents evoked by 100 µM kainic acid (KA) and by anti-GluR3 antibody (S) in two different neurons. Anti-GluR3 antibody evoked reproducible currents in a subset of neurons (A1), but little current was evoked by the anti-GluR3 antibody in other neurons (A2). In (B), it is shown that control rabbit sera containing antibodies raised to GluR5 (S1) and nicotinic acetylcholine β2 (S2) subunits did not evoke currents. In (C), it is shown that purified IgG (IgG) fraction and anti-GluR3 antibody serum (S) evoked inward currents whereas serum from which the IgG fraction was removed (S-IgG) did not. In (D), it is shown that peak current response to anti-GluR3 antibody was dilution dependent. In (E), it is shown that reduction of anti-GluR3 antibody-evoked currents by 40 µM CNQX (S+CNQX) was not voltage dependent, as shown in neurons voltage clamped at −75 mV (E1) or +75 mV (E2). In (F), it is shown that anti-GluR3 antibody-evoked currents were not blocked by 10 µM MK-801 (S+MK-801). In (G), it is shown that anti-GluR3 antibody-evoked currents were blocked by GluR3 receptor specific peptide to region GluR3B (S+Peptide B), but not by peptide to region GluR3A (S+Peptide A). Serum without GluR3 peptide also evoked current in this neuron.

Anti-GluR3 antibody-containing sera that had undergone filtration in "AMICON" filters (3,000 M.W. to 50,000 M.W. cutoff, repeated 4 times) to remove glutamate and other small molecules were diluted into external solution for direct application to neurons. Miniperfusion of either rabbit 5209 serum (diluted 1:8) or the 5209 IgG fraction to voltage clamped neurons resulted in rapid and reversible non-desensitizing inward currents in a subset of neurons (FIG. 4). The number of positively responding cells tended to increase with the age of the culture and peak amplitudes of currents also tended to increase with age of the culture (2–5 weeks).

Average evoked whole cell current in positively responding neurons was 0.48±0.02 (mean±S.E.M.) nanoamps (nA) with a maximum of 1.6 nA (17 of 38 kainic acid responsive cells). The results with serum from rabbit 5210 were similar but required greater serum concentration than rabbit 5209 (see below). The amplitudes of antibody evoked currents were variable between cells when compared with 100 μM kainic acid. Overall, the relative potency of 1:8 diluted anti-GluR3 antibody was less than that of 100 μM kainate (9.8±4.4%; 17 cells) (FIG. 4, A1). All cells responding to antibody responded to kainic acid. Similar experiments using control rabbit serum did not evoke currents. At 1:8 dilution, serum from rabbits containing GluR3 preimmune serum antibodies, antibodies prepared to a portion of GluR5 comparable to GluR3, or antibodies to neuronal nicotinic acetylcholine receptor β2 subunit did not evoke inward currents in 3, 11, and 6 cells, respectively (FIG. 4, B).

Anti-GluR3 serum and total IgG fraction, prepared according to E. Harlow & D. Lane, *Antibodies: A Laboratory Manual* (1988), both activated the GluR receptor, but with different kinetics (FIG. 4, B). Anti-GluR3 serum from which IgG was removed failed to evoke glutamate receptor currents (FIG. 4, C).

Antibody-evoked currents were dilution dependent, with the relative potencies compared to 1:8 serum dilution being 38±13% at 1:16, 19±9% at 1:32, and 5±4% at 1:64 (FIG. 4, D). To test the specificity of anti-GluR3 antibody activity on glutamate receptors, rabbit serum (1:8) was mixed with glutamate receptor antagonists. Antibody-evoked currents were reduced to 4±2% of control by 40 µM of the non-NMDA receptor antagonist, CNQX (6 cells) (FIG. 4, E1). The NMDA receptor antagonist MK-801 (10 µM) had no effect (FIG. 4, F). Blockage of antibody-evoked currents by CNQX was rapid, reversible, and voltage independent (FIG. 4, E2), suggestive of a competitive antagonist mechanism of inhibition. To further test the specificity of the antibody-evoked current responses, 0.5 mg/ml of the GluR3 specific peptides denoted GluR3A (SEQ ID No. 1) or GluR3B (SEQ ID No. 2) were incubated with serum containing anti-GluR3 antibody or IgG for 15 minutes and then applied to neurons. The mixture containing GluR3B peptide blocked the antibody-evoked currents but GluR3A peptide did not block antibody-evoked currents (FIG. 4, G). Like CNQX, blockage of antibody-evoked currents by GluR3B peptide was rapid, reversible, and voltage independent.

Taken together, these results, that serum from rabbit 5209 exhibited greater immunoreactivity to GluR3B than serum from rabbit 5210 (FIG. 3), that serum from rabbit 5209 is more active as an agonist than serum from rabbit 5210, and that the GluR3B peptide blocked antibody-evoked currents when GluR3A did not, indicate that the GluR3B region of GluR3 is the main immunologic region and likely site of ligand-binding and receptor activation for the non-NMDA receptor.

Figure 5:
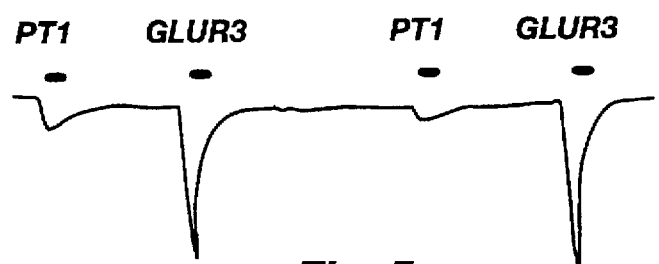
FIG. 5 shows whole cell currents evoked by anti-GluR3 antibody (GLUR3) and by serum from a Rasmussen's encephalitis patient (PT1) recorded from voltage-clamped fetal mouse cortical neurons in culture.
Figure 6:
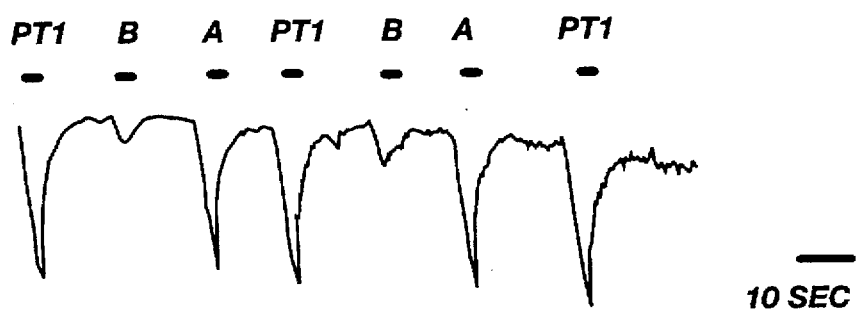
FIG. 6 shows blocking by GluR3B synthetic peptide (B), but not by GluR3A peptide (A), of whole cell currents evoked by serum from a Rasmussen's encephalitis patient (PT1).

These conclusions are supported by additional electrophysiological experiments conducted with serum from patients having Rasmussen's encephalitis. For example, FIG. 5 shows the results of one (PT1) of 5 Rasmussen's encephalitis patients wherein the patient's serum is able to activate glutamate receptor currents, similar to the ability of rabbit anti-GluR3 serum (GLUR3) to activate currents. Further, as shown in FIG. 6, the GluR3B synthetic peptide (B) blocks currents evoked by serum from a Rasmussen's encephalitis patient, whereas the GluR3A synthetic peptide (A) does not.

The finding that the potential ligand binding site of a GluR is in the region of sequence diversity (such as peptide GluR3B) was unexpected. In other receptor systems, such as GABA, nicotinic acetylcholine, and glycine receptors, the potential ligand binding site and region of receptor activation is highly conserved in sequence both between subunits of the same family and among the receptors of the general ligand-activated superfamily.

Paraneoplastic Disease

Human paraneoplastic syndrome refers to a collection of diseases that result from remote complications of a systemic cancer rather than from a direct result of complications from a tumor mass or metastases. Paraneoplastic disorders may affect a variety of tissues including bone marrow, joints, or kidneys, but are best known for those forms that effect the central nervous system (CNS). Paraneoplastic syndrome in the brain is characterized by highly specific neurodegeneration, such as loss of Purkinje neurons, variable loss of granule cells, and occasional perivascular lymphocytic infiltrates. High titer anticerebellar antibodies are common and patients are often incapacitated by the loss of neuronal function rather than from the progression of the tumor. Neurological symptoms generally precede finding the tumor, which is most frequently in the lung, ovary, or breast. As many as 16% of patients with lung cancer have been reported to exhibit neurodegeneration.

The mechanism of cancer-related neurodegenerative disease is not well defined but is thought to occur through an autoimmune process. Hence, in the progression of an immune response to a tumor, an antigen or a protein that contains or mimics an epitope normally expressed in the CNS is presented on the tumor and an antibody response is mounted. In this case, however, antibodies attack the antigen on neurons in the brain, which is believed to result in neuronal death. There is no effective treatment for the neurodegenerative aspect of this disease, although anti-CNS antibodies may decrease after removal of the tumor.

Paraneoplastic disease is divided into two major groups based on the tumor type and antibody response. Type 1 is associated with gynecological and breast tumors and with "anti-yo" antibodies. Type 2 is almost exclusively associated with lung and breast cancers and with "anti-Hu" or "anti-Ri" immunoreactivity. Anti-yo, -Hu, and -Ri refer to immunoreactivity to a defined set of poorly characterized antigens that are observed on immunoblots of neuronal membrane preparations. Recently, the sera of 16 patients with Type 1 or Type 2 paraneoplastic disease were examined for autoimmune reactivity to neuronal glutamate receptor (GluR) subunits.

One patient (patient 1) was identified with Type 1 paraneoplastic disease whose serum exhibited highly specific immunoreactivity on immunoblots to a bacterial fusion protein containing a sub-portion of the GluR5 subunit. immunohistochemical analyses of mouse brain sections using serum from this patient, however, revealed specific regional staining of limbic system structures (e.g. hippocampus and lateral septum) and Purkinje cells of the cerebellum that closely resembled GluR1 immunoreactivity. Subsequent immunocytochemical analysis of cultured cells transfected with a subset of GluR subunits revealed that serum from this patient exhibited reactivity towards GluR1 and GluR6 but not GluR2, GluR3, or GluR4 (GluR5 cannot be tested in this assay). Staining persisted to dilutions of 1:20,000. Together these results suggest that this patient harbors autoantibodies to at least three GluR subunits (GluR1, GluR5, and GluR6).

Figure 7:
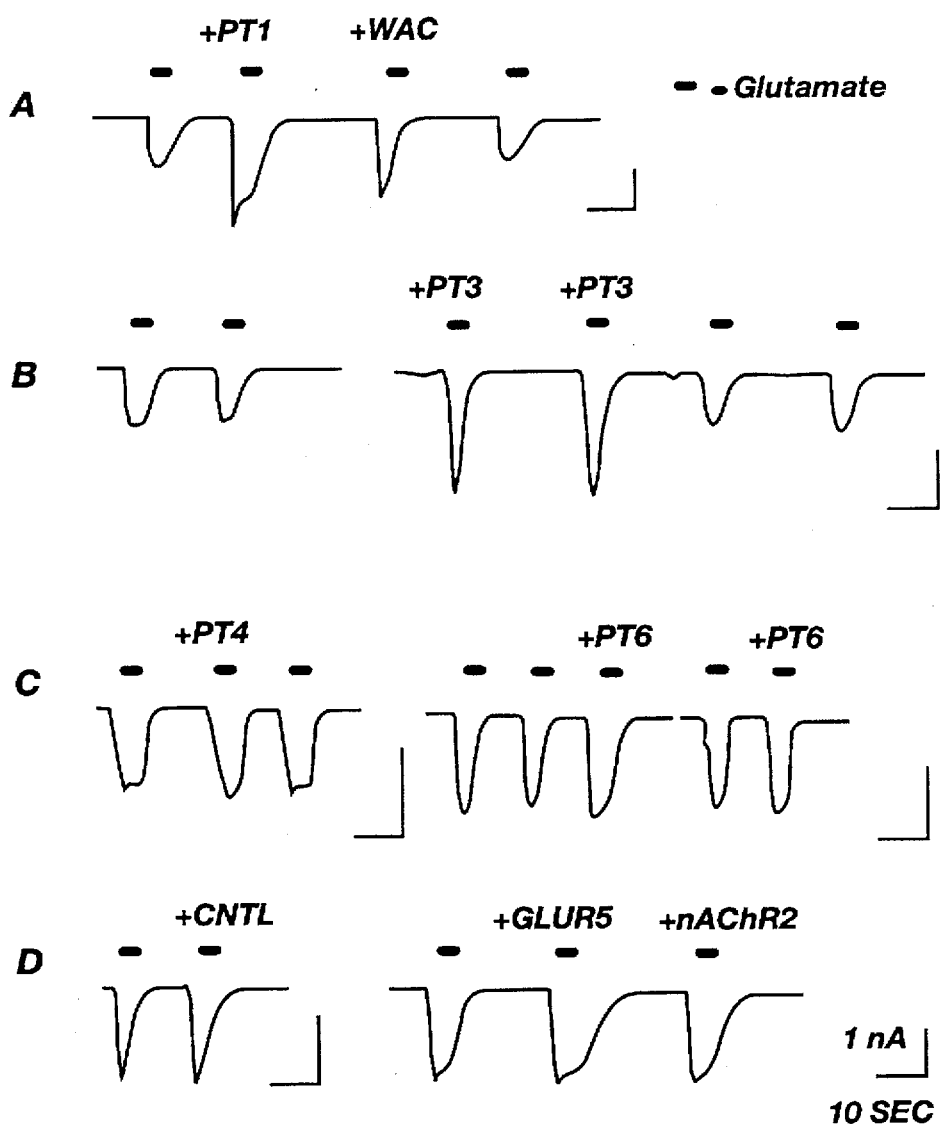
FIG. 7 shows enhancement of glutamate-evoked whole cell currents recorded from voltage-clamped fetal mouse cortical neurons in culture by sera from some paraneoplastic patients and by affinity purified antibody to GluR5, but not by serum from other paraneoplastic patients or controls. The calibration bars are 10 sec and 1 nA throughout, and horizontal bars indicate administration of 100 µM glutamate. In (A), there is shown enhancement of glutamate-evoked currents by serum from patient #1 (PT1) and by affinity purified antibody to GluR5 (WAC) in the same neuron. In (B), there is shown enhancement of glutamate-evoked currents by serum from patient #3 (PT3). In (C), there is shown lack of enhancement of glutamate-evoked currents by sera from patients #4 (PT4) and #6 (PT6). In (D), there is shown lack of enhancement of glutamate-evoked currents by serum from a healthy control patient (CNTL) and by rabbit sera containing antibodies to GluR5 fusion protein (GLUR5) and neuronal nicotinic acetylcholine receptor subunit β2 (nAChR2).

Affinity-purified IgG, S. W. Rogers et al., *The Characterization and Localization of the Glutamate Receptor Subunit, GluR1, in the Rat Brain*, 11 *J. Neurosci.* 2713 (1991), to GluR5 was studied using methods of electrophysiology. These studies showed that this antibody produced an increase in glutamate receptor current when co-applied with glutamate relative to glutamate alone (FIG. 7, +WAC). The antibody alone has no effect on receptor function. This result suggests that affinity-purified anti-GluR5 IgG acts to enhance the effect of glutamate, suggesting a direct effect of this antibody on the receptor. Further, as noted above, the excessive activation of these receptors has been linked with the death of cells that contain them. Hence, the antibody effect of enhancing GluR activation is consistent with the selective loss of neurons that are rich in this particular receptor type. Finally, analysis of a portion of the tumor from this patient (metastatic adenocarcinoma of unknown origin) using polymerase chain reaction (PCR) with reverse transcriptase, e.g. U.S. Pat. No. 4,683,292, hereby incorporated herein by reference, revealed the presence of RNA for GluR1 and GluR5 in the tumor.

Examination of 15 additional paraneoplastic cases (see Table 1) revealed immunoreactivity toward various GluR's in 12 of 16 patients.

TABLE 1

| Patient | E-P[a] | Assay[b] | GluR1 | GluR2 | GluR3 | GluR4 | GluR5/6 |
|---|---|---|---|---|---|---|---|
| 1 | Yes[c] | TC | + | – | – | – | + |
|  |  | IB | – | – | – | – | + |
| 2 | None | TC | – | – | – | – | – |
|  |  | IB | – | – | – |  |  |
| 3 | Yes | TC | – | – | – | + | – |
|  |  | IB | – | – | – | – |  |
| 4 | None | TC | + | – | – | – | – |
|  |  | IB | – | – |  |  |  |
| 5 | Yes | TC | + | – | + | +? | + |
|  |  | IB | – | – | – |  |  |
| 6 | None | TC | – | – | +? | – | + |
|  |  | IB | – | – | – |  | – |
| 7 | Yes | TC | – | – | – | – | +? |
|  |  | IB | – | – | – |  | – |
| 8 | None | TC | – | – | – | – | – |
|  |  | IB | – | – | – |  | – |
| 9 | NT[d] | TC | + | – | – | – | – |
|  |  | IB | – | – | – | – | – |
| 10 | NT | TC | + | – | – | – | – |
|  |  | IB | – | – | – |  |  |
| 11 | NT | TC | + | +? | – | – | + |
|  |  | IB | – | – | – |  | – |
| 12 | NT | TC |  |  |  | – | – |
|  |  | IB | – | – | – | – | – |
| 13 | NT | TC | – | – | – | – | – |
|  |  | IB | – | – | – |  |  |
| 14 | NT | TC | + | – | +? | – | – |
|  |  | IB | – | – | – |  |  |
| 15 | NT | TC |  |  | – | + | – |
|  |  | IB | – | – | – |  |  |
| 16 | NT | TC | + | – | + | + | – |
|  |  | IB | – | – | – |  |  |
| 17 | NT | TC |  |  |  |  |  |
|  |  | IB | – | – | – |  | – |
| 18 | NT | TC | – | – | + | – | + |
|  |  | IB | – | – |  |  |  |

[a]Electrophysiology was used to determine whether currents were evoked by exposure to anti-GluR sera.
[b]Assays used were immunocytochemistry after transforming cells with GluR cDNAs (TC) and immunoblots (IB).
[c]Strong currents were evoked.
[d]Not tested by methods of electrophysiology.

No immunoreactivity was observed in two healthy controls included in this blind study. Of this mixed immunoreactivity, 8 of 12 contained immunoreactivity to GluR1, and 5 of 12 contained immunoreactivity to GluR5 and/or GluR6. Examination of the first 8 patients using methods of electrophysiology revealed that in addition to the patient described above (patient 1), additional patients (for a total of 4 of 8 in this sample) also enhanced the effect of glutamate on GluR's. Patient 8 was a control. interestingly, 3 of the 4 samples that enhanced GluR current labeled positive to GluR6 in the transfected cell assay. In the remaining case, serum immunoreactivity to tested GluR's was not found (weak reactivity to GluR4) suggesting that this patient harbors immunoreactivity to GluR subunits that have not yet been tested (we test for 7 of these at the present time) or the target subunit has not yet been cloned. Also evident from this study is the advisability of examining serum from patients by at least two methods: an immunoblotting or histochemical approach and a functional approach. Combined, these methods allow for a rapid screening for immunoreactivity to GluR's and the more involved functional study both confirms the likelihood of an antibody that affects receptor function and reduces the number of false negatives or positives.

FIG. 7 shows that mixing serum from some paraneoplastic neurodegenerative syndrome patients (PT1, PT3) with glutamate (100 μM) enhances currents evoked by glutamate alone, but serum from other paraneoplastic patients (PT4, PT6; diluted 1:4) or controls does not modulate currents. In (A), it is also shown that affinity purified antibody to GluR5 (WAC; diluted 1:2) also enhanced currents in a neuron that was susceptible to current enhancement by serum from patient #1. In (D), it is shown that serum from a non-diseased control patient (CNTL) and rabbit sera containing antibodies to GluR5 fusion protein (GLURS) or neuronal nicotinic acetylcholine receptor subunit β2 (nAChR2) also failed to enhance glutamate-evoked currents.

These results show that autoimmune reactivity to GluR subunits can occur in victims of cancer and that this autoreactivity may contribute to the remote effect of neurodegeneration. Further, this autoimmune reactivity differs from the anti-GluR3 immunoreactivity observed in Rasmussen's encephalitis, since different GluR subunits are involved, and the antibodies act to enhance glutamate receptor function rather than directly activating the receptor.

Amyotrophic Lateral Sclerosis

Amyotrophic lateral sclerosis (ALS) or Lou Gehrig's disease is a devastating neurological disease that produces relentlessly progressive weakness and paralysis resulting in death without affecting cognition. ALS primarily affects motor neurons of the spinal cord and brain. initial symptoms usually include mild weakness of the extremities and twitching of muscles. The weakness is progressive and eventually involves muscles of the neck, face, and those necessary for breathing. Death occurs in 2–5 years and usually results from respiratory compromise. Pathologically, loss of primary motor neurons responsible for muscle activation are lost in the spinal cord, brainstem, and cortex of the brain. At least two major theories are postulated for the pathophysiologic mechanisms of cell loss in ALS. One originates from the finding that a familial form of ALS has been linked to a gene for superoxide dismutase (SOD), but the familial form accounts for less than 10% of ALS cases, and the etiology of the sporadic form remains unknown. It has been proposed that defective SOD allows the accumulation of oxygen free radicals that damage and eventually kill the cell. The second theory is that cell loss may be associated with excitotoxicity due to activation of glutamate receptors. Supporting evidence for increased excitation has been demonstrated in that passive transfer of ALS patient IgG increased neuromuscular junction miniature end-plate potential frequencies of recipient mice. Recently, it has been reported that antibodies to a calcium channel protein has been found in 8 of 12 ALS patients studied. F. Kimura et al., 35 Annals Neurol. 164 (1994). This finding of an autoimmune process involved in ALS is supported by previous reports showing IgG in motor neurons and inflammatory cells within the motor neuron regions of spinal cord and brain. However, what role these calcium channel antibodies play in the pathophysiologic mechanism of ALS remains unclear and these may represent a secondary immune process associated with the disease.

TABLE 2

| Patient | Assay* | GluR1 | GluR2 | GluR3 | GluR4 | GluR5/6 |
|---|---|---|---|---|---|---|
| S.B. | TC | – | + | – | – | – |
|  | IB | – | + | – |  | – |
| E HUL | TC | – | + | – | – | + |
|  | IB | + | + | – |  | + |
| RER | TC | – | + | – | – | – |
|  | IB | – | + | – |  | – |
| SEL | TC | +? | +? | – | – | +? |
|  | IB | – | + | – |  | + |
| SSK | TC | – | + | – | – | +? |
|  | IB | – | + | – |  | + |

TABLE 2-continued

| Patient | Assay* | GluR1 | GluR2 | GluR3 | GluR4 | GluR5/6 |
| --- | --- | --- | --- | --- | --- | --- |
| TEG | TC | – | – | – | – | +? |
|  | IB | – | + | – |  | – |
| H-C | IB | – | + | – |  | – |
| KBC | IB | – | – | – |  | – |
| JPP | IB | – | – | – |  | – |
| CEV | IB | – | + | – |  | – |

*Assays used were immunocytochemistry after transforming cells with GluR cDNAs (TC) and immunoblots (IB).

Table 2 summarizes the data collected from patients diagnosed with ALS, wherein 8 of 10 patients exhibited autoantibodies to the GluR2 subunit. In 3 or 4 of 8 patients, immunoreactivity to GluR5 and/or GluR6 was also present. Except for patient SEL, who exhibited very weak immunoreactivity to GluR1 in cells transfected with GluR1, no immunoreactivity to GluR1, GluR3, or GluR4 has been confirmed in these patients. These results suggest that in contrast to Rasmussen's encephalitis (anti-GluR3) and paraneoplastic neurodegenerative disorder (predominantly anti-GluR1 and anti-GluR5 and/or GluR6); patients tested for ALS exhibit predominantly GluR2 immunoreactivity, with a subset of the patients exhibiting GluR5 and/or GluR6 autoreactivity. Examination of the serum from patient S.B. using methods of electrophysiology revealed results similar to those obtained in paraneoplastic disease.

Figure 8:
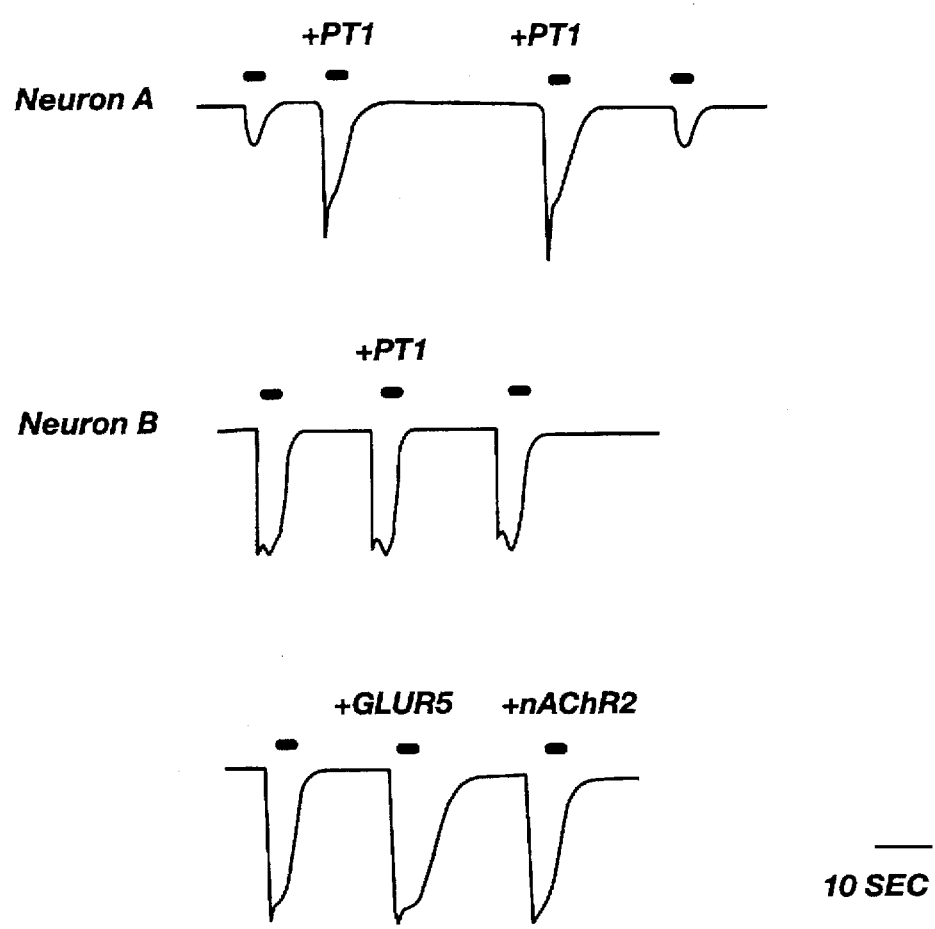
FIG. 8 shows enhancement of glutamate-evoked whole cell currents by serum from an ALS patient (PT1) in one neuron (Neuron A), but not in another neuron (Neuron B). Antibodies prepared in rabbits to the entire fusion protein of GluR5 (GLUR5) and nicotinic acetylcholine receptor (nAChR2) also fail to modulate glutamate receptor currents. The solid bars indicate administration of glutamate.

Whole cell recordings from mouse cortex neurons in culture revealed that glutamate evoked currents in most neurons. A subset of neurons responded with an enhancement of the glutamate-evoked current when co-applied with serum from ALS patient S.B. (FIG. 8). This effect was rapid and reversible, similar to that which may be seen with a drug that modulated glutamate receptor function. Not all neurons were observed to show modulation by the serum. This finding indicates glutamate receptor specificity for certain neurons and needs to be explored further. Rabbit antibodies to an unknown region of GluR5 and rabbit antibodies to a nicotinic receptor protein (nAChRβ2) do not modulate glutamate-evoked currents (FIG. 8).

Neurodegenerative Disease of Unknown Diagnosis

Some patients exhibit progressive or devastating neurological deterioration without known cause. Others are seen to suffer neurodegenerative disease without an etiologic diagnosis. Other neurological diseases are associated with nervous system destruction or dysfunction and appear to be correlated with peripheral signs of inflammation, immune response or temporally related to infection (para- or post-infectious syndromes). Some of these include Sydenham's Chorea in children (St. Vitus Dance), Gullian-Barre syndrome, and post-infectious encephalomyelitis. The possibility exists that some of these syndromes may be due to antibody-directed attack on receptor/ion channel proteins in neurons or glial cells.

We recently studied two brothers, ages 19 and 22, who both developed severe seizures, encephalopathy, and inflammatory changes in multiple brain areas on MRI scan. One brother's serum exhibited highly specific immunoreactivity on immunoblots to bacterial fusion proteins of glutamate receptor subunit GluR6. The other brother exhibited immunoreactivity to GluR5 and GluR6.

Collectively these studies support the conclusion that autoantibodies to specific glutamate receptors occur in numerous neurodegenerative diseases and can serve as diagnostic markers. Further, electrophysiology studies contribute to the conclusion that some of these antibodies may act directly upon the receptor to alter its function. In other autoimmune diseases where autoantibodies to the antigen alter its function (e.g., autoantibodies to the muscle nicotinic acetylcholine receptor in myasthenia gravis or to the thrombin receptor of the thyroid gland in Grave's disease), the antibodies have proven to be directly related to the pathogenesis of the disease. These observations suggest that neurotransmission systems in the brain are targets of autoimmune disease. The correlation of autoimmunity to specific receptors with specific neurodiseases provides physicians with a diagnostic marker that gives a quantitative end-point for diagnosis, e.g., immunoblot, immunocytochemistry of transfected cells, ELISA, immunohistochemical analysis on tissue sections, immunodiffusion assays (e.g., Ouchterlony plate assay, radioimmunoassay, rocket immunoelectrophoresis) and suggests that therapeutic intervention of severe neurodegenerative disease can be accomplished through methods of autoimmune therapy.

In Vitro Diagnostics

The following methods provide an estimate of antibody titer to glutamate receptors in patients with neurological disease. A biological sample, such as a blood sample, of less than 1 ml is adequate for the assays.

The establishment of a correlation between the presence of circulating autoimmune antibodies towards neuronal glutamate receptor subunits and a seizure-related disorder such as Rasmussen's encephalitis (RE), paraneoplastic neurodegeneration disease (PND), or amyotrophic lateral sclerosis (ALS) presents a unique and novel approach to diagnose these and other related diseases. For example, ALS is currently diagnosed on the basis of symptoms such as fatigue, muscle weakness, and advanced electromyogram changes. Screening of serum from ALS patients for autoreactive antibodies offers physicians an accurate and sensitive assay with a defined endpoint for diagnostic application. Suitable assays for such screening of serum include immunoblot assay, immunohistochemistry of transfected cells, ELISA, competitive peptide ELISA, immunohistochemical analysis on tissue sections, immunodiffusion assays (e.g., Ouchterlony plate assay, radioimmunoassay, rocket immunoelectrophoresis), and the like. The extension of an assay to include a functional test (e.g., electrophysiology) offers the additional advantage of inferring the relationship of autoantibody to disease pathology. A finding of a positive result by these screening methods indicates that a patient has or is at risk for the disorder or syndrome being screened.

EXAMPLE 1

Immunoblot Analysis of Portions of Neurotransmitter Receptors Expressed as Proteins by Bacteria Fusion proteins containing corresponding regions of the putative extracellular domain from glutamate receptor subunits GluR1, GluR2, GluR3, GluR4, GluR5, GluR6, GluRKA2, NMDAR1 and NMDAR2, neuronal nicotinic acetylcholine receptor subunits $\alpha1$, $\alpha2$, and $\beta2$, and gamma-aminobutyric receptor channels $\alpha1$, $\alpha2$, $\alpha6$, $\beta1$, $\beta2$, and $\gamma2$, and the neuronal glycine receptor (as well as any inotropic or metabotropic neurotransmitter receptor that may be selected for testing) are prepared in bacteria by any number of available bacterial fusion protein over-production systems. Proteins are prepared according to methods for the bacterial fusion protein system of choice, enriched, fractionated by SDS-PAGE, and transferred to nitrocellulose. An example of how this can be done using any of many variations of immunoblot technology is presented. Each immunoblot is blocked (e.g., with 2 percent dry milk in phosphate buffered saline (blotto)) for 1 hour at room temperature, and then incubated with agitation in blotto supplemented with a portion of the patient serum to a final dilution of between 1:50 to 1:1000 overnight at 4° C. Blots are then rinsed in PBS 5 times over a period of 45 minutes, and incubated in blotto containing goat anti-human IgG+ IgM conjugated with alkaline phosphatase at 1:750 for 1 hour at room temperature. Blots are again rinsed in PBS as before, then rinsed in developing buffer containing 50 mM Tris, 100 mM NaCl, and 2 mM $MgCl_2$ twice, pH 9.5. Immunoreactivity is then visualized by placing the blots in developing buffer containing 1 µg/ml nitro blue tetrazolium (NBT) and 0.5 µg/ml 5-bromo-4-chloro-3-indolyl phosphate (BCIP). Developing proceeds for approximately 15 minutes before PBS is used to stop the reaction. Positively staining bacterial fusion proteins appear as dark lavender to blue bands. Controls include normal human serum (negative control) and rabbit serum from animals that have been immunized with the appropriate subunit protein (positive control for transfection and chemistry).

These assays are relatively easy to perform and can be conducted on a large scale. They may produce false negatives either because the entire receptor protein is not present in the fusion protein or the receptor protein is not in its native state (folded and glycosylated).

EXAMPLE 2

Immunocytochemistry of Transfected Cells

Cultured cells that are transiently transfected with cDNAs encoding neurotransmitter receptor subunits are used routinely to screen antisera for its subunit-specificity. Many methods are available for this procedure. The following is an example of one of these. This procedure is described in terms of the GluR's but is routinely done for all neurotransmitters of interest.

Mammalian expression vector constructs (CMV-based promoter system) containing cDNAs that encode each GluR subunit, respectively, are prepared, DNA isolated and transfected into human embryonic kidney (HEK) 293 cells, which are particularly susceptible to transient transfection, using standard methods such as calcium phosphate precipitation. J. Sambrook et al., *Molecular Cloning: A Laboratory Manual*, (2d ed., 1989). The incubator atmospheric $CO_2$ is then reduced from 5% to 3%, culture is allowed to proceed for 24 to 48 hours, and cells are prepared for immunocytochemical detection of transfected antigen using serum samples. One serum sample on 12 different subunits or 12 serum samples on one subunit are screened in duplicate in 24-well dishes. To test for immunoreactivity, cultured cells are washed gently and fixed with freshly prepared 2% paraformaldehyde in 0.1 M cacodylate buffer (pH 7.4) for 30 minutes at room temperature. PBS can be substituted for cacodylate buffer. The fixative is removed, the cells washed gently with PBS. The cells are then permeabilized using blocking PBS (PBS with 1% heat inactivated normal horse or goat serum) containing 0.2–0.4% Triton X-100 for 30 minutes at room temperature. Cells are then washed in blocking PBS. Serum diluted to the working concentration with blocking PBS is then added to the cells and incubated overnight at 4° C. After the overnight incubation, cells are rinsed with PBS at least 4 times over a 45 minute period at room temperature. The secondary antibody (e.g., alkaline phosphatase-conjugated goat anti-human or horseradish peroxidase (HRP)-conjugated goat anti-human) is then diluted in blocking PBS (e.g., 1:500) and then added to the cells for 1 hour at room temperature. For alkaline phosphatase the following development scheme is used.

The cells are washed with three changes of PBS, twice with 50 mM Tris, 100 mM NaCl, and 2 mM $MgCl_2$ (pH 9.5) and the alkaline phosphatase visualized by developing the cells at room temperature in the same buffer with freshly added NBT (0.5 mg/ml) and BCIP (0.25 mg/ml). Development is usually for 10 to 30 minutes with fresh developing solution added every 10–15 minutes. To stop the reaction, PBS supplemented with 2 mM EDTA is used. Plates are then read for the presence of cells exhibiting dark blue staining (usually 10–40%). Controls include normal human serum (negative control) and rabbit serum from animals that have been immunized with the appropriate subunit protein (positive control for transfection and chemistry).

Some patients exhibit autoreactivity to cellular proteins such as nuclear or mitochondrial proteins that interfere with the specificity of the assay and can lead to false positives. To minimize this problem, sera are first adsorbed against HEK293 cells that have not been transfected. An example of this method is as follows. HEK293 cells are grown to confluency in 150 mm culture dishes, fixed, permeabilized, and placed in blocking PBS as described above. The antiserum is diluted to the working concentration (1:1000 to 1:3000) in blocking PBS (final volume of approximately 5 ml) and then incubated with agitation across the monolayer of HEK293 cells for 1 hour at room temperature. This "pre-cleared" antiserum is then added to the cells of interest for the overnight incubation at 4° C. as described above.

These assays are relatively easy and can be conducted on a large scale. They are generally more reliable and more sensitive than immunoblots. They are, however, labor intensive and can require up to one week to obtain results.

EXAMPLE 3

Enzyme Linked ImmunoSorbent Assay (ELISA)

ELISA assays are the most sensitive, rapid, and economical method to screen serum for anti-receptor immunoreactivity. They suffer from the potential of false negatives, again because the full receptor protein in the native conformation is difficult to obtain for screening. An insect cell/baculovirus over-expression system, J. Sambrook et al., *Molecular Cloning: A Laboratory Manual* (1989), is presently being used to compensate for this limitation. This system offers the advantage of being able to produce relatively large portions of the receptor protein (i.e., entire extracellular domain) that is glycosylated and is folded in its proper conformation. This protein is secreted by cultured insect cells into the culture medium where it is enriched and purified by standard methods, e.g. J. Sambrook et al., *Molecular Cloning: A Laboratory Manual* (2d ed., 1989); F. Ausubel et al., *Current Protocols in Molecular Biology* (1987), hereby incorporated by reference. The protein can then be affixed to an ELISA dish as an antigen.

This is a general outline of the methodology used for ELISA analysis of serum protein from patients for autoreactivity to neuroreceptors. Fusion proteins are used for general screens of serum. Peptide screens are done to determine specific epitope immunoreactivity in the serum. In all assays, proteins are adsorbed quantitatively to "IMMULON" ELISA dishes. "IMMULON 2" dishes are preferred for fusion protein analysis. Antigen in 50 µl PBS aliquots at a concentration of 1 ng/well to 1 µg/well is added to each of 96 wells on the ELISA dish and allowed to adsorb overnight at 4° C. in a humidified chamber. The antigen is removed and then each well is blocked for non-specific protein adsorption with 50 µl of 3% BSA/0.02% Tween 20 (block solution) for 2 to 4 hours at room temperature or overnight at 4° C. Plates are then washed with PBS/0.02% Tween 20 with an IMMULON washer and the serum sample to be tested is then added to a subset of wells at two dilutions (e.g., 1:750 and 1:1500) in block solution. Incubation at room temperature for 2 hours is generally sufficient. Plates are then washed and secondary antibody (peroxidase-conjugated anti-human antibody diluted to 1:7500 in PBS) is added for 1 hour at room temperature. Plates are washed with PBS at least 8 times and developed with the peroxidase chromophore ABTS (1,1'-azino-bis(3-ethylbenzthioline-6-sulfonic acid); Sigma Chemical Co., St. Louis, Mo.; 1 mg/ml in McIlvaine's buffer (phosphate/citrate buffer, pH 4.6) and 0.005% $H_2O_2$). E. Harlow & D. Lane, supra. Development is monitored at 405 nm on an ELISA reader. Positive controls include rabbit anti-serum to the antigen, and negative controls include unaffected human control serum and BSA.

EXAMPLE 4

Competitive Peptide ELISA

A competitive peptide ELISA assay can also be used to determine the specificity of immunoreactivity in a serum sample. This assay is performed according to the procedure of Example 3 except that synthetic peptides that are likely antigens in these diseases can be added with the primary antibody on dishes where fusion protein of the respective receptor is absorbed to the dish. Comparing the measurement of serum immunoreactivity in the presence and absence of peptide allows for a determination of the relative complexity of serum immunoreactivity.

EXAMPLE 5

Screening of Autoantibodies for Potential Pathogenicity: Alteration or Modulation of Receptor Function in Cultured Neuronal Cells Currently, the composition of native GluR's and GABAR's is unknown and the potential diversity of native receptors is immense. To assay the modulatory capability of antibodies, cultured neuronal cells are used for electrophysiological testing on native receptors. Use of cortical neurons offers the most diverse expression of receptors of interest for testing. For more unique or limited receptor expression, cultured neurons from hippocampus, basal ganglia, cerebellum, spinal cord, retina, or peripheral ganglia may be used. Whole cell and excised patch clamp recording is used to measure direct activation or modulation of GluR's or GABAR's in these cells. Solutions are designed to isolate sodium or calcium current flux for GluR's and chloride flux for GABAR's and to block other receptors and ion channels. Two major paradigms are used. First, antibody is applied by miniperfusion (0.5–10 sec) directly to the cell or patch to evaluate direct action of the antibody on receptors. Second, current response (control) to application of glutamate or more specific GluR agonists such as kainate, AMPA, or NMDA is compared to subsequent response (test) to application of the agonist plus antibody. Time is allowed for wash out of agonist and antibody during continuous superperfusion of the culture dish. A subsequent application (wash) of agonist is performed to assess persistence of antibody effect. This procedure is repeated in the same cell until cell death or breakdown of the recording. Five cells are recorded for each paradigm and antibody. initial test concentration is a 1:4 dilution of purified serum (AMICON filtered to remove molecules of 3,000 M.W. to 50,000 M.W.). Statistical analysis of whole cell currents is a two-tailed t-test of the control vs. test peak current and steady state current, wash vs. test peak current and steady state current, and average ((control+wash)/2) vs. test peak current and steady state current. Analysis is done with spreadsheets. Pharmacological specificity is assayed using receptor specific antagonists such as MK-801 or CNQX. These antagonists are added to the antibody-containing solution and tested using the paradigms described above. Antigenic specificity is tested with receptor specific peptides constructed from studies described above.

EXAMPLE 6

Screening of Autoantibodies for Potential Pathogenicity: Antibody Activation of Neuronal Receptors Expressed in *Xenopus Oocytes* injected with cRNA to Express the Receptor of Choice and Known Subunit Composition More specific assays of functional receptor protein and antibody interaction involve the use of expressed receptor proteins in non-neuronal mammalian cells and *Xenopus oocytes*. An advantage to this approach is that receptor composition is defined and specific antibody protein interactions can be tested. Another advantage is that RNA isolated from whole brain or a subregion of the brain can be injected directly into the non-neuronal cell or oocytes so that receptors are made from all possible combinations, including those that either have not been cloned or are unique to a region of the brain. This approach allows for a very broad screen that can later be narrowed to greater specificity using cRNAs.

For example, receptors composed of only GluR3 protein can be expressed and studied in isolation. initial assays use cRNAs injected into *Xenopus oocytes*. E.g., E. Butler & M. Chamberlain, 257 J. Biol. Chem. 5772–78 (1982); D. Melton et al., 12 Nucleic Acids Res. 7035–56 (1984). Two electrode voltage clamp methods measure antibody-evoked currents or antibody-modulated agonist currents using paradigms outlined above. These recordings are easier to perform than those with neurons and require less operator expertise. Agonist, antibody, and drug delivery also are simplified by using a superperfusion system, but delivery is considerably slower. Testing protocols are similar and assessment is performed using similar statistical analysis on 5 or more oocytes. Since the Xenopus expression system uses a non-mammalian cell, receptor expression may be different than that for mammalian cells. For this reason, additional detailed testing is performed on transiently transfected human embryonic kidney cells using whole cell recording techniques. Testing paradigms are the same as those for the neurons.

EXAMPLE 7

Screening of Autoantibodies for Potential Pathogenicity: Cell Death

Cultured cells can be used as a rapid method to measure the impact of patient serum cell death. Cultured cortical cells or cells transfected with selected receptor cDNA(s) are subdivided into a control group (no serum addition) or groups that receive continuous exposure to two concentrations of patient serum (e.g., 1:100 and 1:500) for 24 to 36 hours. The culture medium from these cells is then removed and assayed for release of lactate dehydrogenase (LDH, kit assays are routinely used for this assay) to the medium. Cells treated with cytotoxic agents serve as the positive control for cell death, and normal human or known receptor excitotoxic compounds (e.g., kainic acid or NMDA) are used as internal standards for measurements. Trypan blue exclusion staining of cells allows a visual conformation of cell viability and death. Trypan blue is taken up and imparts a blue color intracellularly to dead cells.

EXAMPLE 8

Monitoring Treatment for Neurological Disorders and Neurodegenerative Syndromes

At present, numerous methods are used to treat autoimmune disease. For example, patients with multiple sclerosis, myasthenia gravis, or rheumatoid arthritis may be treated with plasmapheresis, steroids, chemotherapy (such as with cytoxan, i.e., methotrexate), or others. E.g., C. A. Bona et al. eds., *The Molecular Pathology of Autoimmune Diseases* (1993). In all cases, little is known regarding the actual site of immunoreactivity of antibodies on the target molecule, and long-term prognosis for the patient is poor. Antibody reactivity to a specific portion of the receptor molecule (e.g., peptide ELISA) that is involved in the disease and is potentially pathogenic can now be measured directly. This offers clinicians the capability of determining if a specific autoimmune therapy is affecting the titer of the "pathogenic" autoantibody rather than irrelevant autoantibodies or the total IgG pool.

Thus, a method of monitoring a neurological disorder or neurodegenerative syndrome wherein autoantibodies to one or more neuronal glutamate receptor subunits are associated therewith comprises the steps of collecting a biological sample from a patient who is to be treated, determining the amount of anti-GluR antibodies in the sample, treating the patient for the disorder or syndrome, collecting another sample from the patient, determining the amount of anti-GluR antibodies in the second sample, and comparing the amounts determined in the samples. The samples can be any biological fluid that contains sufficient amounts of antibodies for detection and quantitation, such as blood, blood plasma, cerebrospinal fluid, and the like. Typically, a 1 ml sample is sufficient for making such a determination according to methods described herein. Methods for quantitating the amounts of anti-GluR antibodies in the sample include immunoblots, ELISA, transfected cell assays, immunohistochemical analysis on tissue sections, immunodiffusion assays (e.g., Ouchterlony plate assay, radioimmunoassay, rocket immunoelectrophoresis, Jan Klein, *Immunolog* (1982)), and the like and electrophysiological measurements.

Comparison of the pre- and post-treatment amounts of anti-GluR antibodies indicates whether the treatment is effective in reducing the antibodies being monitored. If it is, then continued monitoring of the amounts of antibodies aids the health care provider in knowing if or when additional treatment is needed. If the treatment is not effective, then the health care provider is alerted that a change of treatment may be needed.

Drug Development

GluR's are central to learning and memory and in various diseases are related to initiation of neuronal malfunction, damage, and death. This implies that identification of an active site or sites on GluR's will directly contribute to development of drugs to intercede or controllably enhance these patho-physiological processes, e.g., improve learning or memory.

Autoantibodies that recognize and bind GluR fusion proteins provide evidence for two modes of action on the receptor and, hence, two different activities of the protein. First, the ability of serum from Rasmussen's encephalitis patients to directly activate the receptor is evidence of one such mode of action or activity. The GluR3B peptide localizes the site of direct activation. Second, serum from paraneoplastic patients or ALS patients enhances or modulates the effect of glutamate on the receptor. This suggests that an additional site, not yet completely mapped but within the confines of the portion of the receptor contained in the fusion protein, modulates the receptor function. Such modulation is similar to that observed for drugs such as barbiturates (e.g. phenobarbital, pentobarbital, secobarbital, thiopental, etc.) or benzodiazepines (e.g. chlordiazepoxide, diazepam, and oxazepam, etc.) on the GABA receptor. No such drugs have been identified for the GluR receptor.

A gross difference in the kinetics of activation of the receptor by anti-GluR3 whole serum and the IgG fraction thereof also has implications for drug development. Referring to FIG. 4 C, whole serum opens the receptor and maintains the current until the serum is removed. Kinetically, this phenomenon resembles the effect of the non-NMDA GluR agonist, kainic acid. IgG, however, produces an effect where the receptor opens and then closes, even in the presence of continuous application of IgG. This effect is referred to as "desensitization" and more closely resembles the effect of AMPA. These observations demonstrate that the manner in which antibody is prepared can result in a different pharmacological response on the same receptor. The implications are that an agonist that produces a sustained response is more likely to be pathogenic through the production of an excitotoxic effect. Also, this will allow the specific nature of an antibody-antigen reaction to be studied at the structural level to ascertain the nature of what produces the differential effect.

EXAMPLE 9

Drug Development

The identification of a 24 amino acid region of GluR3 that is bound by an antibody that activates or alters receptor function suggests strongly that this site acts in the ligand-binding site or modulatory site of this receptor. Further, the peptide alone can compete with the receptor for agonist to reduce the efficacy of agonist for receptor activation. This means that this region can be used to target for drug development and peptides to this region may be used as tools for both drug development and as potential therapeutics.

Peptides can be used to compete with potential agonists in an assay where receptor activation or modulation is the end point measurement. For example, if an agonist at 4 μM activates the receptor, ritering into the agonist a peptide of known concentration would allow determination of the agonist affinity and efficacy for binding and activation of receptor (competition assay). This could be used to screen for potential drugs that would be specific to the receptor.

Drug affinity for peptides coupled to beads can be measured to determine whether a drug binds or does not bind the peptide. Similarly, the drug could be added in the presence of a known agonist to determine the potential for displacement of this agent. Such an assay would suggest the specificity of a drug for the receptor (different peptides=different receptor subunit) and would allow a simple way to screen many drugs rapidly and evaluate their potential for further testing in functional assays such as effects on receptor activation or blocking cell death.

EXAMPLE 10

A method of treating a patient afflicted with Rasmussen's encephalitis comprises systemically administering an effective amount of a peptide capable of binding anti-GluR3 autoantibodies and blocking autoantibody-evoked activation of the GluR3 subunit. Such a peptide comprises the GluR3B peptide (SEQ ID NO:2) and peptides substantially homologous thereto. Such substantially homologous peptides could include the GluR3 fusion protein or the entire GluR3 receptor. In general, however, smaller peptides are preferred. The GluR3B peptide is synthesized as described above. A sterile preparation of an effective amount of the GluR3B peptide is then injected into or otherwise systemically administered to a Rasmussen's encephalitis patient.

---

We claim:
1. A peptide for blocking autoantibody-evoked activation of GluR3 in neuronal cells consisting of a sequence of amino acids represented by SEQ ID NO:2.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
 ( A ) LENGTH: 29 amino acids
 ( B ) TYPE: amino acid
 ( D ) TOPOLOGY: linear ( x i ) SEQUENCE DESCRIPTION: SEQ ID NO:1:

```
Asn Asn Glu Asn Pro Met Val Gln Gln Phe Ile Gln Arg Trp Val Arg
 1               5                  10                  15
Leu Asp Glu Arg Glu Phe Pro Glu Ala Lys Asn Ala Pro
                 20                  25
```

( 2 ) INFORMATION FOR SEQ ID NO:2:

( i ) SEQUENCE CHARACTERISTICS:
 ( A ) LENGTH: 24 amino acids
 ( B ) TYPE: amino acid
 ( D ) TOPOLOGY: linear ( x i ) SEQUENCE DESCRIPTION: SEQ ID NO:2:

```
Asn Glu Tyr Glu Arg Phe Val Pro Phe Ser Asp Gln Gln Ile Ser Asn
 1               5                  10                  15
Asp Ser Ser Ser Ser Glu Asn Arg
                 20
```

( 2 ) INFORMATION FOR SEQ ID NO:3:

( i ) SEQUENCE CHARACTERISTICS:
 ( A ) LENGTH: 29 amino acids
 ( B ) TYPE: amino acid
 ( D ) TOPOLOGY: linear ( x i ) SEQUENCE DESCRIPTION: SEQ ID NO:3:

```
Asn Tyr Thr Asp Thr Ile Pro Ala Arg Ile Met Gln Gln Trp Arg Thr
 1               5                  10                  15
Ser Asp Ser Arg Asp His Thr Arg Val Asp Trp Lys Arg
                 20                  25
```

( 2 ) INFORMATION FOR SEQ ID NO:4:

( i ) SEQUENCE CHARACTERISTICS:
 ( A ) LENGTH: 29 amino acids
 ( B ) TYPE: amino acid
 ( D ) TOPOLOGY: linear ( x i ) SEQUENCE DESCRIPTION: SEQ ID NO:4:

```
Asp Tyr Asp Asp Ser Leu Val Ser Lys Phe Ile Glu Arg Trp Ser Thr
 1               5                  10                  15
Leu Glu Glu Lys Glu Tyr Pro Gly Ala His Thr Ala Thr
                 20                  25
```

( 2 ) INFORMATION FOR SEQ ID NO:5:

( i ) SEQUENCE CHARACTERISTICS:

-continued (A) LENGTH: 25 amino acids
        (B) TYPE: amino acid
        (D) TOPOLOGY: linear (xi) SEQUENCE DESCRIPTION: SEQ ID NO:5:

Asn Glu Asp Asp Lys Phe Val Pro Ala Ala Thr Asp Ala Gln Ala Gly
 1           5                  10                  15
Gly Asp Asn Ser Ser Val Gln Asn Arg
            20              25

(2) INFORMATION FOR SEQ ID NO:6:

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO:6:

Ser Glu Val Asp Lys Met Val Val Thr Leu Thr Glu Leu Pro Ser Gly
 1           5                  10                  15
Asn Asp Thr Ser Gly Leu Glu Asn Lys
            20              25